United States Patent [19]

Inamoto et al.

[11] 4,111,990
[45] Sep. 5, 1978

[54] 1-ACETYLAMINOTRICYCLO [4.3.1.1$^{2,5}$] UNDECANE AND PROCESS FOR THE PREPARATION THEREOF

[75] Inventors: Yoshiaki Inamoto; Koji Aigami; Motoyoshi Ohsugi; Yoshiaki Fujikura; Hiroshi Ikeda, all of Wakayama, Japan

[73] Assignee: Kao Soap Co., Ltd., Tokyo, Japan

[21] Appl. No.: 839,976

[22] Filed: Oct. 6, 1977

[30] Foreign Application Priority Data

Oct. 12, 1976 [JP] Japan .................................. 51-122440

[51] Int. Cl.$^2$ .................. C07D 102/08; C07D 103/12
[52] U.S. Cl. .............................................. 260/561 R
[58] Field of Search ..................................... 260/561 R

[56] References Cited

U.S. PATENT DOCUMENTS

| 3,352,912 | 11/1967 | Prichard | 260/561 R X |
| 3,523,136 | 8/1970 | Schneider et al. | 260/561 R X |
| 3,523,137 | 8/1970 | Moore | 260/561 R X |
| 3,579,567 | 5/1971 | Deslongchamps | 260/561 R X |

*Primary Examiner*—Allen B. Curtis
*Attorney, Agent, or Firm*—Blanchard, Flynn, Thiel, Boutell & Tanis

[57] ABSTRACT

1-Acetylaminotricyclo [4.3.1.1$^{2,5}$] undecane is prepared by reacting either (a) 1-substituted tricyclo [4.3.1.1$^{2,5}$] undecane, wherein the substituent is Cl, Br or OH, or (b) endo-2-hydroxymethyl-exo-2,3-trimethylenenorbornane with acetonitrile, in the presence of sulfuric acid. 1-Acetylaminotricyclo [4.3.1.1$^{2,5}$] undecane is useful as an intermediate to prepare antiviral substances.

4 Claims, No Drawings

1-ACETYLAMINOTRICYCLO [4.3.1.1$^{2,5}$] UNDECANE AND PROCESS FOR THE PREPARATION THEREOF

BACKGROUND OF THE INVENTION

1. Field of the Invention

The present invention relates to 1-acetylaminotricycloundecane and processes for the preparation thereof.

More particularly, the present invention relates to 1-acetylaminotricyclo [4.3.1.1$^{2,5}$] undecane of formula (I) and processes for the preparation of this compound by reacting a tricyclo [4.3.1.1$^{2,5}$] undecane derivative of formula (II) or endo-2-hydroxymethyl-exo-2,3-trimethylenenorbornane of formula (III) with acetonitrile in the presence of sulfuric acid:

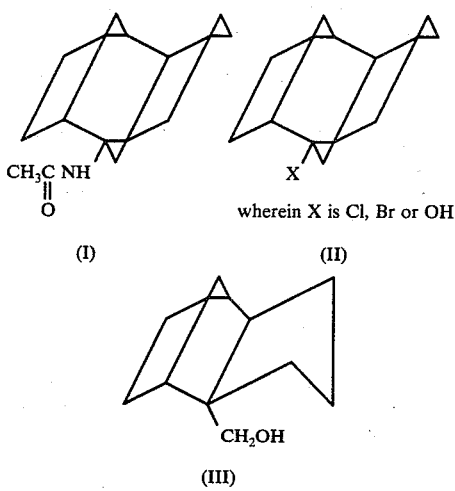

wherein X is Cl, Br or OH

1-Acetylaminotricyclo [4.3.1.1$^{2,5}$] undecane of formula (I) which is the desired product of the present invention is very useful as an intermediate. If this compound is hydrolyzed and then the corresponding amino derivative thus obtained is neutralized with hydrochloric acid, 1-aminotricyclo [4.3.1.1$^{2,5}$] undecane hydrochloride is obtained which has a strong antiviral activity and which is very useful as an ingredient of medicines for human beings and animals.

Elementary analysis and mass spectrum analysis of 1-acetylaminotricyclo [4.3.1.1$^{2,5}$] undecane synthesized according to the present invention proves that this is a compound containing only one nitrogen atom. The structure of the compound has been confirmed from the fact that the absorptions peculiar to amide (3325, 1650, 1550 cm$^{-1}$) appear in the infrared absorption spectrum.

In the preparation of the compound of formula (I) of the present invention, a tricyclo [4.3.1.1$^{2,5}$] undecane derivative of formula (II) or endo-2-hydroxymethyl-exo-2,3-trimethylenenorbornane of formula (III) is used as the starting compound and it is reacted with acetonitrile in the presence of sulfuric acid.

Acetonitrile is used in an amount of 1 to 100 moles, preferably 10 to 50 moles, per one mole of the starting compound. Sulfuric acid is used in an amount of 1 to 20 moles, preferably 5 to 10 moles, per one mole of the starting compound. The concentration of the sulfuric acid is in the range of 80 to 100%, preferably 90 to 100%. The reaction temperature is in the range of from −20° C to 82° C, preferably 20° to 50° C. Under the above reaction conditions, the reaction is completed in 24 hours. Although there can be used any inert solvent which does not adversely affect the reaction, it is preferred to carry out the reaction without a solvent in view of the ease of after-treatment.

If the tricyclo [4.3.1.1$^{2,5}$] undecane derivative of formula (II) is used as the starting compound, the reaction which takes place is the so-called Ritter reaction.

If endo-2-hydroxymethyl-exo-2,3-trimethylenenorbornane of formula (III) is used as the starting compound, isomerization of the skeleton and the Ritter reaction take place simultaneously. A process of converting endo-2-hydroxymethyl-exo-2,3-trimethylenenorbornane (III) into a compound possessing the tricyclo [4.3.1.1$^{2,5}$] undecane skeleton by acid catalytic isomerization reaction has been proposed by two of the inventors and another author Lukaishi et al, "J. Chem. Soc." Perkin Trans., 1, 789 (1975)). The present invention has been accomplished on the basis of the discovery that if said reaction is carried out in the presence of acetonitrile, the Ritter reaction also immediately takes place to form 1-acetylaminotricyclo [4.3.1.1$^{2,5}$] undecane, according to the following reaction scheme:

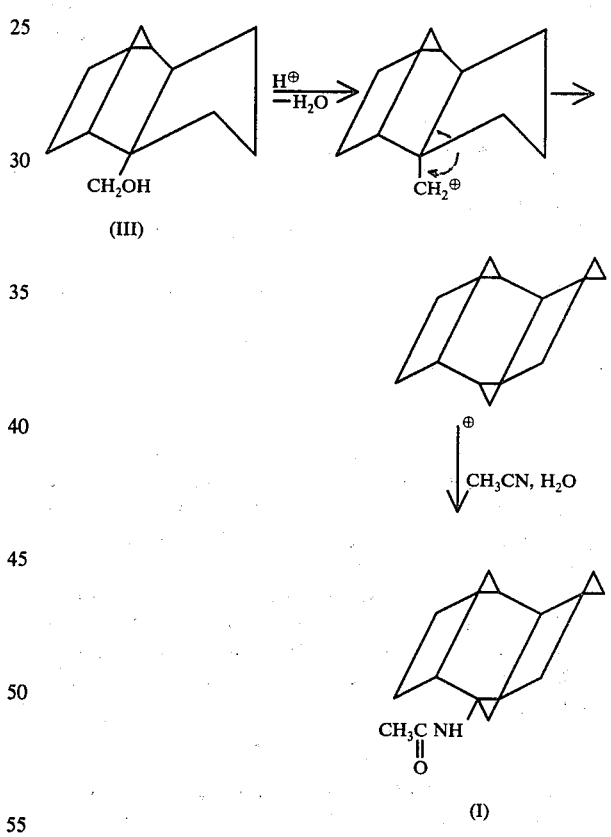

1-Bromotricyclo [4.3.1.1$^{2,5}$] undecane used as a starting compound of formula (II) in the present invention can be synthesized by, for example, brominating tricyclo [4.3.1.1$^{2,5}$] undecane with liquid bromine or by brominating tricyclo [4.3.1.1$^{2,5}$] undecane-1-ol with thionyl bromide. 1-Chlorotricyclo [4.3.1.1$^{2,5}$] undecane can by synthesized by chlorinating tricyclo [4.3.1.1$^{2,5}$] undecane-1-ol with thionyl chloride. Tricyclo [4.3.1.1$^{2,5}$] undecane-1-ol can be synthesized by hydrolyzing 1-chloro- or 1-bromotricyclo [4.3.1.1$^{2,5}$] undecane or by isomerizing endo-2-hydroxymethyl-exo-2,3-trimethylenenorbornane in aqueous sulfuric acid solution.

Endo-2-hydroxymethyl-exo-2,3-trimethylenenorbornane used as the starting compound of formula (III) can be obtained easily by, for example, reacting exo-2,3-trimethylene-5-norbornene or exo-6-hydroxy-exo-2,3-trimethylenenorbornane with formic acid or carbon monoxide in sulfuric acid to effect esterification, thereby forming endo-2-carboxy-exo-2,3-trimethylenenorbornane (H. Koch & W. HAAF, "Ann." 638, 111 (1960)) and then reducing the ester (Lakanishi et al "J. Chem. Soc.", Perkin Trans., 1, 789 (1975)).

The following examples further illustrate the present invention.

EXAMPLE 1

10.0 Grams (60 millimoles) of tricyclo [4.3.1.1$^{2,5}$] undecane-1-ol (X=OH in formula (II)) are dissolved in 120 ml of acetonitrile. The solution is cooled and kept at 0° C, and then 25 ml of concentrated sulfuric acid are added dropwise under stirring over 45 minutes. The stirring is continued further at room temperature for 5 hours. The reaction mixture is placed onto 200 g of ice and extracted twice, each time with 100 ml of diethyl ether. The combined extracts are washed with saturated aqueous solution hydrogencarbonate solution and then with water and dried with anhydrous sodium sulfate. The solvent is distilled out and the residue is recrystallized from acetone-n-hexane to obtain 12.2 g (yield 98%) of 1-acetylaminotricyclo [4.3.1.1$^{2,5}$] undecane (I) as white crystals (m.p. 138°–139° C).

Elementary analysis: Found: C, 75.21; H, 10.20; N, 6.34%. Calculated (as $C_{13}H_{21}NO$): C, 75.36; H, 10.14; N, 6.76%.

IR (KBr, cm$^{-1}$): 3325, 3070, 1680, 1650, 1550, 1470, 1370, 1310, 1280, 1125

Mass spectrum m/e (relative intensity) 207 (14, M$^+$), 164 (45), 138 (100), 96 (8), 87 (12)

EXAMPLE 2

1.18 Grams (5.1 millimoles) of 1-bromotricyclo [4.3.1.1$^{2,5}$] undecane (X=Br in formula (II)) are dissolved in 10 ml of acetonitrile. The solution is cooled and kept at 0° C, and then 2.5 ml of concentrated sulfuric acid are added dropwise under stirring over 30 minutes. The stirring is continued further at room temperature for 20 hours. The reaction mixture is treated in the same manner as described in Example 1 to obtain 0.98 g (yield 92%) of 1-acetylaminotricyclo [4.3.1.1$^{2,5}$] undecane.

EXAMPLE 3

10.0 Grams (60 millimoles) of endo-2-hydroxymethyl-exo-2,3-trimethylenenorbornane are dissolved in 120 ml of acetonitrile. The solution is cooled and kept at 0° C, and then 25 ml of concentrated sulfuric acid are added dropwise under stirring over 45 minutes. The stirring is continued further at room temperature for five hours. The reaction mixture is placed on 200 g of ice and extracted twice, each time with 100 ml of ether. The combined extracts are washed with saturated aqueous solution of sodium hydrogencarbonate and then with water and dried with anhydrous sodium sulfate. The solvent is distilled out and the residue is recrystallized from acetone-n-hexane to obtain 12.2 g (yield 98%) of 1-acetylaminotricyclo [4.3.1.1$^{2,5}$] undecane (I) as white crystals.

PREPARATION 1

1.0 Gram (4.8 millimoles) of tricyclo [4.3.1.1$^{2,5}$] undecane is added to 2 ml (38.7 millimoles) of liquid bromine and the whole is stirred at room temperature for 17 hours. The reaction mixture is added slowly to a cooled saturated solution of sodium hydrogensulfite under stirring to remove excess bromine. The aqueous solution is extracted twice, each time with 20 ml of carbon tetrachloride, and the combined extracts are dried with magnesium sulfate. Carbon tetrachloride is distilled out and the residue (1.9 g) is distilled under reduced pressure to collect a fraction boiling at 96°-8° C/2mmHg to obtain 1.0 g (yield 65.5%) of 1-bromotricyclo [4.3.1.1$^{2,5}$] undecane. Upon cooling, white crystals of a melting point of 57.5° to 58.5° C are obtained.

Elementary analysis: Found: C, 57.2; h, 7.4; Br, 34.2%. Calculated (as $C_{11}H_{17}Br$): C, 57.7; h, 7.5; Br, 34.9%.

IR (Nujol, cm$^{-1}$): 3030, 1295, 1240, 1155, 1060, 1000, 995, 960, 760.

$^1$HNMR (CDCL$_3$ solvent, TMS internal standard): 0.8 and 2.8 (multiplet)

$^{13}$CNMR (CDCl$_3$ solvent, TMS internal standard, c): 22.46(t), 26.52(t), 27.98(t and t), 34.27(t), 37.77(d), 39.35(t), 39.80(d), 41.18(t), 51.41(d), 75.08(s).

Mass spectrum m/e (relative intensity): 230 (0.1, M$^+$), 228 (0.2, M$^+$), 150 (13), 149 (100), 107 (15), 91 (15), 83 (18), 81 (44), 79 (23), 67 (8).

PREPARATION 2

10 Grams (4.4 millimoles) of 1-bromotricyclo [4.3.1.1$^{2,5}$] undecane are dissolved in acetone-water (145 ml – 95 ml) and the solution is refluxed under stirring for one hour. After allowing the solution to cool, the solution is extracted with petroleum ether and the extract is dried with anhydrous magnesium sulfate. The solvent is distilled out. The residue is purified by sublimation to obtain 0.69 g (yield 95%) of tricyclo [4.3.1.1$^{2,5}$] undecane-1-ol as white crystals.

Melting point: 79 to 80° C

Elementary analysis: Found: C, 79.4; H, 10.6 Calculated as $C_{11}H_{18}O$: C, 79.5; H, 10.8.

IR (Nujol, cm$^{-1}$): 3280, 3030, 1480, 1465, 1340, 1090, 1075, 1035, 945.

Mass spectrum m/e (relative intensity): 166 (0.3, M$^+$), 123 (57), 98 (7), 97 (100), 95 (23), 81 (5), 79 (9), 77 (5).

PREPARATION 3

A solution of 40 g (0.24 mole) of endo-2-hydroxymethyl-exo-2,3-trimethylenenorbornane (III) in 100 ml of carbon tetrachloride is added to 400 ml of cooled 50% aqueous sulfuric acid solution. Then, the solution is stirred at room temperature for 35 hours and the reaction mixture is extracted three times, each time with 200 ml of diethyl ether. The extract is washed with saturated aqueous solution of sodium hydrogencarbonate and then with water. The ether solution is dried with anhydrous sodium sulfate and ether is distilled out. After purification by sublimation, 39.2 g (yield 98%) of tricyclo [4.3.1.1$^{2,5}$] undecane-1-ol are obtained as white crystals of a melting point of 79° to 80° C.

Additional details of the preparation of the formula (II) compounds are disclosed in Japanese Ser. No. 120983/76, filed Oct. 7, 1976, corresponding to U.S. Ser. No. 833,679, filed Sept. 15, 1977 the entire contents of which are incorporated herein by reference.

The embodiments of the invention in which an exclusive property or privilege is claimed are defined as follows:

1. 1-Acetylaminotricyclo [4.3.1.1$^{2,5}$] undecane having the formula (I):

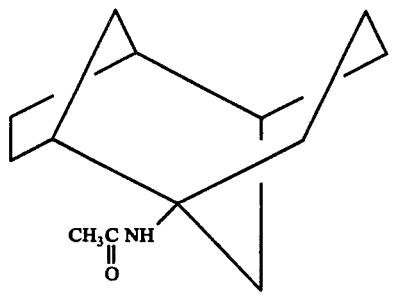

(I)

2. A process for preparing 1-acetylaminotricyclo [4.3.1.1$^{2,5}$] undecane which comprises reacting endo-2-hydroxymethyl-exo-2,3-trimethylenenorbornane of formula (III) with acetonitrile in the presence of sulfuric acid:

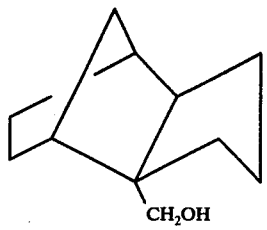

(III)

3. A process for preparing 1-acetylaminotricyclo [4.3.1.1$^{2,5}$] undecane according to claim 2 wherein 1 to 100 moles of acetonitrile and 1 to 20 moles of sulfuric acid are used per one mole of said endo-2-hydroxymethyl-exo-2,3-trimethylenenorbornane.

4. A process for preparing 1-acetylaminotricyclo [4.3.1.1$^{2,5}$] undecane according to claim 2 wherein the reaction temperature is in the range of from −20° to 82° C.

* * * * *